United States Patent
Fauconet et al.

(10) Patent No.: US 6,281,386 B1
(45) Date of Patent: Aug. 28, 2001

(54) PURIFICATION OF ACRYLIC ACID OBTAINED BY CATALYTIC OXIDATION OF PROPYLENE

(75) Inventors: Michel Fauconet, Valmont; Marc Esch, Freyming Merlebach; Denis Laurent, Saint-Avold, all of (FR)

(73) Assignee: Atofina, Paris (FR)

( * ) Notice: Subject to any disclaimer, the term of this patent is extended or adjusted under 35 U.S.C. 154(b) by 0 days.

(21) Appl. No.: 09/308,756

(22) PCT Filed: Nov. 20, 1997

(86) PCT No.: PCT/FR97/02092

§ 371 Date: May 25, 1999

§ 102(e) Date: May 25, 1999

(87) PCT Pub. No.: WO98/23573

PCT Pub. Date: Jun. 4, 1998

(30) Foreign Application Priority Data

Nov. 25, 1996 (FR) .................................................. 96 14397

(51) Int. Cl.[7] .................................................. C07C 51/42
(52) U.S. Cl. ............................................................. 562/600
(58) Field of Search .............................................. 562/600

(56) References Cited

U.S. PATENT DOCUMENTS 3,932,500 * 1/1976 Duembgen et al. .
6,166,248 * 12/2000 Heida et al. .

FOREIGN PATENT DOCUMENTS 2449780A 4/1976 (DE) .
2196986A 3/1974 (FR) .

* cited by examiner

*Primary Examiner*—Paul J. Killos
*Assistant Examiner*—Robert W. Deemie
(74) *Attorney, Agent, or Firm*—Millen, White, Zelano & Branigan, P.C.

(57) ABSTRACT

The method consists in extracting acrylic acid by counter-current filtration washing of reaction gases by at least a hydrophobic absorbing heavy solvent, then recuperating the purified acrylic acid from the solution obtained at the end of this extracting step. As hydrophobic absorbing heavy solvent at least a hydrophobic aromatic compound is used having: a boiling point under atmospheric pressure between 260° C. and 380° C.; a crystallisation temperature less than 35° C. and a viscosity less than 10 mPa·s in a range of temperature between 30–80° C.

17 Claims, 1 Drawing Sheet

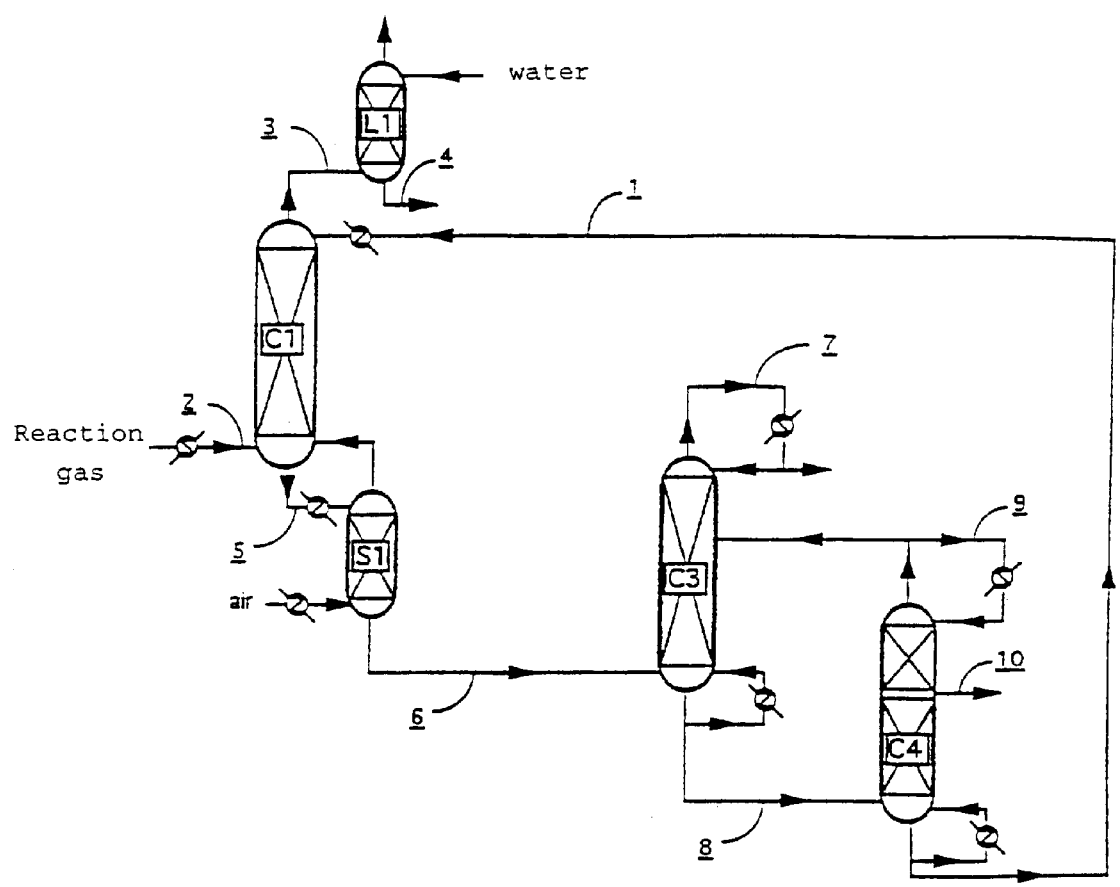

PURIFICATION OF ACRYLIC ACID OBTAINED BY CATALYTIC OXIDATION OF PROPYLENE

The present invention relates to the purification of acrylic acid.

The main route for the synthesis of acrylic acid used industrially today is the catalytic oxidation of propylene, which generates acrolein as an intermediate. This reaction, which takes place in the gas phase, generates a gas flow mainly comprising, in addition to acrylic acid, non-condensable gases: unconverted propylene, nitrogen, carbon monoxide and dioxide, "light" organic compounds, that is to say for which the boiling point is less than that of acrylic acid: steam, unconverted acrolein, impurities manufactured by side reactions: formaldehyde, acetic acid, and, finally, heavy compounds: maleic anhydride, furfuraldehyde, benzaldehyde, and the like.

The processes for the purification of this reaction gas which are described in the literature consist in condensing this mixture and in extracting the organic compounds by countercurrent washing using water or heavy solvents.

Processes using an absorption with water exhibit the disadvantage of extracting in a not very selective way virtually all the organic products present in the gas mixture. The purification of the aqueous solution thus composed requires difficult and expensive separations by distillation and/or extraction.

French Patent No. 1,558,432 discloses a process which consists in absorbing the organic compounds present in the reaction gas using esters of aliphatic or aromatic acids with high boiling points or tributyl or tricresyl phosphate. On conclusion of this absorption stage, the light products (acrolein, formaldehyde) are removed at the top of a first distillation column and a second distillation column makes it possible to obtain, at the top, a more concentrated aqueous acrylic acid solution than in the prior art. However, the subsequent purification of the solution obtained, which still comprises acetic acid and water, still requires expensive separations.

The process disclosed in French Patent No. 2,002,126 introduces an improvement by virtue of the use of a mixture of fractions with high boiling points, recovered at the bottom of the columns for the purification of the esters manufactured from acrylic acid, mainly comprising maleates, polyacrylic acids or polyacrylates. This process makes it possible to clear in a single stage, at the top of a distillation column, most of the compounds with low boiling points, such as acrolein, formaldehyde, water and acetic acid. However, this process for the manufacture of acrylic esters is ill-suited to the production of pure acrylic acid, in particular because of the presence, in the initial crude acrylic acid mixture, of esterification derivatives recycled in the absorption stage.

An improvement is introduced into the process using an extraction with the help of heavy hydrophobic solvents, such as disclosed in French Patent No. 2,146,386, German Patent No. 4,308,087 and European Patent No. 706,986, which makes it possible to obtain, on conclusion of the extraction stage, an anhydrous solution which has been freed from a substantial portion of the light organic products which constituted the initial gas mixture (acrolein, formaldehyde, acetic acid), thus substantially facilitating the subsequent purification of the acrylic acid.

French Patent No. 2,146,386 discloses the use of a hydrophobic solvent having a boiling temperature greater than 170° C. at atmospheric pressure and a viscosity of less than 10 cSt in a temperature range of 30–80° C. and in particular the use of a mixture of diphenyl (DP) and diphenyl ether (DPO) as absorption solvent, with in particular approximately 25% by weight of DP and 75% by weight of DPO. This mixture forms a eutectic (at a concentration by mass of 26.5% of DP and 73.5% of DPO) which exhibits the advantage of having a lower solidification point (S=12° C.) than DPO alone (M.p.=27° C.).

It is well known that the distillation of acrylic monomers and in particular of acrylic acid, which readily polymerize under the effect of radicals formed by a thermal effect, for example, requires the use of polymerization inhibitors, particularly during the distillation stages. Compounds typically used for this purpose are, for example, phenol derivatives, such as hydroquinone or hydroquinone methyl ether (p-methoxyphenol), or phenothiazine and its derivatives, or derivatives of the thiocarbamates family, or compounds with nitroso groups, or quinones, or aromatic amines.

In the examples of French Patent No. 2,146,386, the inhibitor involved is phenothiazine. Unfortunately, the application of the process described according to this patent results in the distillation equipment being fouled by polymeric impurities, which finish by causing blockages of the plant.

To reduce this problem, German Patent No. 4,308,087 discloses the use of an absorption solvent composed of the eutectic mixture of DP and DPO, and of dimethyl phthalate (DMP), at a content of 0.1 to 25% by weight in the total mixture.

European Patent No. 706,986 discloses, in these examples, the use of the DP+DPO eutectic mixture and of a mixture of 80% by weight of this binary+20% by weight of DMP.

The mixtures using DMP exhibit two major disadvantages:

DMP is markedly less hydrophobic than the DP+DPO mixture. In the presence of 10% by weight of acrylic acid in the solvent (conditions approximating to the process), the solubility of water in the DP+DPO mixture is approximately 0.1% by weight, against approximately 4% for DMP. Now, the presence of water in the process is inevitable, since this impurity is generated in the initial oxidation reaction of propylene, resulting in acrylic acid. It follows that the flow recovered at the absorption column bottom is much richer in water and in acetic acid since the water, by affinity, increases the absorption of acetic acid in the solvent flow, which complicates the subsequent purifications. This disadvantage is naturally found in the process disclosed in French Patent No. 2,196,986, which discloses the use of carboxylic esters as absorption solvents, since, according to this process, acetic acid and water are absorbed at the same time as acrylic acid;

in the presence of water, DMP is subject to a hydrolysis side reaction which is promoted by the thermal level of the absorption stage. This side reaction results in the formation of novel impurities, such as phthalic anhydride and methanol, which reacts with acrylic acid to form the corresponding ester (methyl acrylate). Besides the additional difficulties related to the separation of these impurities, this esterification reaction results in a loss of acrylic acid.

The same disadvantage, related to the side reaction of hydrolysis of the solvent, exists for all hydrolysable compounds, in particular those of the esters family. The process disclosed in French Patent No. 2,196,986, which claims the use, as absorption solvents, of heavy carboxylic esters having a melting point of less than 30° C. and a boiling point of greater than 160° C., therefore exhibits this same disadvantage.

Another disadvantage of the DP+DPO mixture is the fact that it is composed of two different compounds which possess a slightly different boiling temperature:

DP: B.p.=255° C. at atmospheric pressure,

DPO: B.p.=258° C. at atmospheric pressure.

In a process as disclosed in French Patent No. 2,146,368 and German Patent No. 4,308,087, the hydrophobic heavy solvent is recycled in the absorption stage, after removal of the light impurities absorbed, recovery of the acrylic acid, purging the intermediate heavy compounds (the boiling temperature of which is between that of the solvent and that of acrylic acid) and purging the heavy compounds (polymerization inhibitors and impurities which have a boiling point greater than that of the solvent).

The removal of the intermediate heavy compounds and of the heavier compounds than the solvent can be carried out by washing with water or by distillation.

The first process exhibits the disadvantage of generating an aqueous effluent which is highly polluted with organic compounds, including the solvent, present at its solubility limit in water. Furthermore, some constituents, which are only slightly soluble in water, are incompletely removed by this method and can accumulate in the recycled solvent loop.

In order to avoid a phenomenon of accumulation of these stabilizers, which are introduced continuously into the distillation columns, the recycling of the solvent in the absorption stage requires the purging of an amount of inhibitors at least equal to that which is introduced into the columns. As the majority of the inhibitors effective in the purification of the monomers sensitive to polymerization have an aromatic structure which renders them only very slightly soluble in water, this process by washing with water is not suitable for their removal.

The second process for the removal of the heavy impurities, by distillation, as disclosed in French Patent No. 2,146,386, requires two separate stages, which are carried out after that of the separation of the acrylic acid:

a stage of distillation of the intermediate heavy impurities (with a boiling point between that of acrylic acid and that of the solvent), in which stage a mixture comprising the intermediate impurities, the main one of which is maleic anhydride, is separated at the top of a column. The main disadvantage of this separation is that, in order to achieve a sufficient purity of the acrylic acid distilled in the preceding purification column, that is to say freed from its heavy impurities, it is necessary to accept that a portion of this monomer will be encountered in the bottom of the said purification column. In the column for the separation of the intermediate heavy impurities, acrylic acid present in this flow is removed with the impurities in question, resulting in an expensive loss. The process disclosed in French Patent Application No. 95-08672, filed on Jul. 18, 1995 on behalf of the Applicant Company, introduces an improvement to this problem by virtue of the removal of the intermediate heavy impurities in a flow drawn up from the side of the column and the recovery, for the purpose of being recycled, of the acrylic acid in the top flow of the same column. However, the processes disclosed in these two patents (FR 2,146,386 and French Application No. 95-08672) exhibit the disadvantage, when the solvent used is a mixture of DP and of DPO, of resulting in a gradual enrichment in the heaviest compound (DPO) in the solvent circulating in the purification loop, due to the difference in the boiling temperatures of the two constituents. In order to maintain a constant composition of the solvent circulating in the purification loop, in order to maintain a steady absorption efficiency and a constant temperature in the columns, it is therefore necessary to carry out an addition of the appropriate amount of the lightest compound (DP), which represents a complicated and expensive operation.

This type of disadvantage is even more of a nuisance in the case of the use of a mixture of DP+DPO and of DMP, as disclosed in German Patent No. 4,308,087, since this process amounts to adding a third compound which has a different boiling temperature (DMP: B.p.=284° C.).

a stage of separation in the heavy impurities, in which stage the compounds with a boiling temperature greater than that of the solvent are removed at the bottom of a distillation column or of an evaporator. This stage is particularly expensive in terms of energy, since it requires distilling a solvent with a high boiling point. The main objective of this stage is to remove the polymerization inhibitors, which are introduced continuously into each of the columns and have to be purged in order to prevent them from accumulating in the loop of solvent to be recycled. Stabilizers effective in the purification of acrylic monomers, such as acrylic acid, exhibit boiling points greater than that of the constituents of the DP+DPO mixture and can consequently only be removed at the bottom of the distillation equipment.

Lastly, a final disadvantage of the DP+DPO mixture is that this liquid mixture solidifies at a temperature of +12° C., which necessitates, to avoid any solidification from taking place when the outside temperature is lower, heating the pipes, equipment and storage tanks carrying the solvent, before recycling in the absorption stage. Due to the large amounts of solvent needed to absorb acrylic acid, this disadvantage can exhibit not insignificant investment and energy costs.

Due to these various disadvantages, related to the use of the solvents claimed in the prior art, the Applicant Company has looked for other hydrophobic solvents, which do not exhibit these difficulties, for the absorption of acrylic acid.

The Applicant Company has surprisingly discovered that ditolyl ether, in the form of a single isomer or of a mixture of isomers, used as aromatic hydrophobic solvent for the absorption of acrylic acid, improves the separations of the impurities present in the reaction mixture. In addition, it transpired during the experimentations that some phenolic stabilizers, which are lighter than this solvent, exhibited a better polymerization inhibiting activity than the inhibitors disclosed in the prior art (such as phenothiazine in French Patent No. 2,146,386). In addition, these compounds can be efficiently removed, in a single stage instead of two stages, with the intermediate heavy compounds, this single stage being less expensive in terms of energy.

Generally, the use for the absorption of acrylic acid of hydrophobic aromatic solvents with a boiling temperature greater than 260° C. preferably in combination with a purification of this monomer in the presence of polymerization inhibitors which are lighter than the solvent, markedly improves the separation of the impurities.

The subject-matter of the present invention is therefore first a process for the purification of acrylic acid obtained by catalytic oxidation of propylene, according to which the acrylic acid is extracted by countercurrentwise washing of the reaction gases with at least one heavy hydrophobic absorption solvent and then the purified acrylic acid is recovered from the solution obtained on conclusion of this extraction stage, characterized in that use is made, as heavy hydrophobic absorption solvent, of at least one hydrophobic aromatic compound having:

a boiling point at atmospheric pressure of between 260 and 380° C., preferably between 270 and 320° C.;

a crystallization temperature of Less than 35° C., preferably of less than 0° C.; and a viscosity of less than 10 mPa·s in a temperature range of 30–80° C.

The hydrophobic aromatic compound is chosen in particular from those represented by the general formulae (I) or (II):

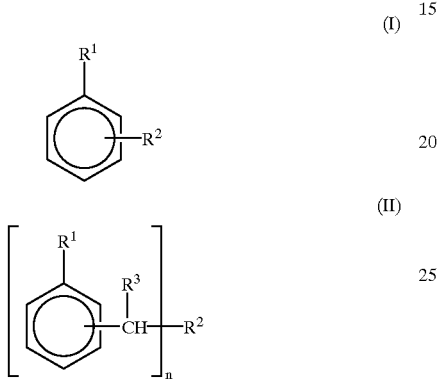

in which:

$R^1$ represents hydrogen, $C_1$–$C_4$ alkyl or cycloalkyl;

$R^2$ represents $C_3$–$C_8$ alkyl, cycloalkyl, —O—$R^4$ (with $R^4$ representing $C_3$–$C_8$ alkyl or cycloalkyl), —O—Ph—($R^5$)—$R^6$ or —Ph—($R^5$)—$R^6$ (with $R^5$ and $R^6$ each independently representing hydrogen or $C_1$–$C_4$ alkyl) (Ph representing a phenylic nucleus);

$R^3$ represents hydrogen or $C_1$–$C_4$ alkyl; and n has the value 1 or 2; and those represented by the general formula (III):

in which:

$R^7$ represents hydrogen or $C_1$–$C_4$ alkyl; and $R^8$ represents $C_1$–$C_4$ alkyl.

The choice is preferably made, from this family, of ditolyl ether in the form of a single isomer or of a mixture of isomers, which exhibits the following advantages:

a single constituent (no problem of separation by distillation);

facilitated separations of the light products (mainly acetic acid) in the absorption-stripping stage and of the heavy products in the following columns;

very low solidification point (−54° C.), which prevents any problem of crystallization in cold weather.

In accordance with a particularly advantageous embodiment of the present invention, the purification of the acrylic acid is carried out after the extraction stage in the presence, when distillations are involved, of a polymerization inhibitor or of a mixture of polymerization inhibitors which is lighter than the absorption solvent, in particular exhibiting a difference in boiling point of greater than 15° C., preferably of greater than 20° C., with the said absorption solvent. These inhibitors are also known hereinbelow as "light polymerization inhibitors". Mention may be made, as examples of these light inhibitors, of p-methoxyphenol, 2,6-di-tert-butyl-p-cresol and 2,4-dimethyl-6-tert-butylphenol.

The process for the purification of acrylic acid according to the invention is furthermore advantageously characterized in that:

a distillation is carried out, in a distillation column (C3), of the flow obtained at the bottom of the extraction column (C1), in which column acrylic acid is extracted by countercurrentwise washing of the reaction gases with the heavy hydrophobic solvent or solvents, the said flow comprising the heavy extraction solvent(s), the desired acrylic acid and impurities, mainly impurities with boiling temperatures greater than that of acrylic acid, the said distillation being carried out under conditions such that a very pure acrylic acid flow is obtained at the top of the said column (C3), acrylic acid being allowed to pass into the bottom;

the bottom flow from the column (C3) is conveyed as feed into the lower part of a distillation column (C4), from the side of which column is drawn off, on a plate situated between the feed and the column top, a flow rich in maleic anhydride and impurities with boiling temperatures situated between that of acrylic acid and that of the said heavy solvent or of the lighter of the said heavy solvents used as a mixture;

a flow rich in acrylic acid is distilled at the top of the column (C4), which flow can advantageously be conveyed to the column (C3); and a flow comprising the said heavy solvent(s) and heavy impurities with boiling temperatures greater than that of the said heavy solvent or of the lighter of the said heavy solvents used as a mixture is recovered at the bottom of the said column (C4), which flow is recycled at the top of the column (C1) for the extraction of acrylic acid present in the reaction gases, the said heavy hydrophobic absorption solvent or solvents being as defined above in the context of the present invention.

Before sending the flow obtained at the bottom of the column (C1) to the column (C3), the said flow can advantageously be freed from a portion of its residual light impurities, such as acetic acid and water, at the top of a column (S1), which can operate as a conventional distillation column equipped with a bottom reboiler or as a stripping column fed at the bottom with a gas (air, inert gas or non-condensed gas mixture recovered at the top of column (C1), or their combination). The gas flow obtained at the top of column (S1), which still comprises acrylic acid, is preferably conveyed to the column (C1).

In accordance with specific embodiments of the process according to the present invention:

the flow obtained at the bottom of the column (C1), if appropriate at the bottom of the column (S1), is conveyed onto a plate situated in the lower half of the column (C3) and the operating point of the said column (C3) is carefully chosen, so as to obtain:

at the top, a flow composed:

predominantly, i.e. at least 95% by weight, of acrylic acid;

the remainder being composed of the heavy compounds: maleic anhydride, furfuraldehyde, benzaldehyde and traces of the heavy extraction solvent(s); and at the bottom, a flow composed of:
predominantly, i.e. at least 95% by weight, of the heavy solvent(s) and of the heavy impurities; the remainder being composed of acrylic acid;
the flow rich in maleic anhydride, heavy impurities and optionally light polymerization inhibitors is drawn off from the side of the column (C4), on an intermediate plate situated above the feed between the lower quarter and the upper quarter of this column, at a temperature chosen so as to obtain a flow with a concentration at least equal to 20% by weight of impurities with boiling temperatures between that of acrylic acid and that of the solvent or of the lighter of the solvents used as a mixture;
the flow distilled at the top of the column (C4), which comprises:
predominantly, i.e. at least 90% by weight, acrylic acid; the remainder being composed of impurities with higher boiling temperatures;
is conveyed to the column (C3) at the level of the main feed of this column or, advantageously, at a level situated above this feed; and
before recycling, at the top of the column (C1), the flow obtained at the bottom of column (C4), the said flow or a portion of the said flow is freed from its heavy impurities with boiling temperatures greater than that of the solvent or solvents, for example by techniques comprising distillation or extraction with the aid of a solvent, optionally used in addition to a thermal dissociation treatment which may or may not involve a catalyst.

In accordance with specific embodiments of the present invention, the distillation is carried out:
in the column (C3), under a pressure of $2.66 \times 10^3$–$3.33 \times 10^4$ Pa (20–250 mm Hg), at a top temperature of 40–120° C. and at a bottom temperature of 120–230° C.; and
in the column (C4), under a pressure of $2.66 \times 10^3$–$3.33 \times 10^4$ Pa (20–250 mm Hg), at a top temperature of 40–120° C., at a bottom temperature of 120–230° C. and at a side draw-off temperature of 40–180° C.

The following Examples illustrate the present invention without, however, limiting the scope thereof. In these examples, the percentages are given by weight. Use was made of distillation columns which are installed according to the diagram in the single FIGURE in the appended drawing, the characteristics of which are indicated below. In the text relating to the description of these examples, the plates of the columns are numbered from the column top (plate 0) to the column bottom (plate n).

Column C1

This column, with a height of 3 m and a diameter of 38 mm, filled with packing elements of multiknit type, is fed:
at the top, with a stream (1) of pure absorption solvent or of absorption solvent recovered at the bottom of column (C4); and
at the bottom, with the stream (2) of reaction gas from the catalytic oxidation of propylene, cooled beforehand to the desired temperature.

A flow (3) is obtained at the top of column (C1) which is rich in light compounds (non-condensable gases, acrolein, formaldehyde, water and acetic acid).

The gas flow (3) is washed with water introduced countercurrentwise into a washing column (L1). An analytical balance of the organic compounds present in the flow (3) is carried out on the flow (4) obtained at the bottom of column (L1).

Column S1

The purpose of the column (S1) is to remove the light compounds present in the bottom of the column (C1) (water, acetic acid, acrolein, and the like). This column, with a height of 1 m and a diameter of 38 mm, is filled with packing elements of multiknit type. It is fed at the top with the bottom flow (5) from column C1, which can be reheated beforehand through an exchanger, and at the bottom with a controlled flow rate of air, the temperature of which is regulated by passing through an exchanger. The gas flow obtained at the top of column (S1) is conveyed to the column (C1) at the level of the feed of the reaction gases into the latter.

At the bottom of column (S1), the recovered flow (6) constitutes a solution in the absorption solvent of acrylic acid with a small portion of the light impurities (acetic acid) and of the heavy impurities initially present in the reaction gas emerging from the oxidation reactor: maleic anhydride, furfuraldehyde, benzaldehyde, compounds from addition to acrylic acid, inhibitors.

The columns (C1), (S1) and (L1) operate at atmospheric pressure.

Column C3

This adiabatic column, equipped with 12 perforated plates, with an efficiency of 9 theoretical plates, is fed at the column base with the flow (6) obtained at the bottom of column (S1). The column is equipped in the lower part with an electrically heated thermosiphon boiler. A portion of the recovered distillate (7), after condensation in a cooler cooled to 18° C., is recycled at the column top in order to provide reflux. Injection of polymerization inhibitor, in solution in acrylic acid, is provided at the condenser top. The assembly operates under a vacuum regulated at $1.33 \times 10^4$ Pa (100 mm Hg)

Column C4

This column is composed of 9 perforated plates with overflow. The feed, via a flow (8) obtained at the bottom of column (C3), is conveyed to the bottom of this column, at the level of the thermosiphon boiler heated by electrical elements. A portion of the condensed distillate (9) is conveyed to the column top to provide reflux. At the level of the 5th plate, a system makes it possible to withdraw as (10) a portion of the condensed liquid phase. This system is equipped with a valve, which is automatically opened when the temperature measured on this plate reaches the set temperature set-point.

The following Examples illustrate the present invention without, however, limiting the scope thereof. In the examples, the percentages of the proportions are by weight.

EXAMPLES

Example 1

The reaction gas mixture (2) obtained at the outlet of reactors for the catalytic oxidation of propylene is cooled through an exchanger to a temperature of 160° C. and then conveyed, at a flow rate of 2160 g/h, to the bottom of the column (C1). The column (C1) receives, at the same level, the gas flow originating from the top of column (S1).

Column (C1) is fed countercurrentwise at the top with (flow 1) 3680 g/h of ditolyl ether at a temperature of 50° C. The ditolyl ether employed is provided in the form of the mixture of isomers having the following composition:

| | |
|---|---|
| 2,2'-dimethyldiphenyl ether (ortho-ortho) | 1.9% |
| 2,3'-dimethyldiphenyl ether (ortho-meta) | 24.8% |
| 2,4'-dimethyldiphenyl ether (ortho-para) | 14.0% |
| 3,3'-dimethyldiphenyl ether (meta-meta) | 30.0% |
| 3,4'-dimethyldiphenyl ether (meta-para) | 24.9% |
| 4,4'-dimethyldiphenyl ether (para-para) | 4.5% |

The liquid mixture collected at the bottom of column (C1) (5) is subsequently conveyed to the top of the column (S1) at a temperature regulated at 120° C.

A flow rate of air of 580 l/h at a temperature of 50° C. is introduced at the bottom of column (S1). The gas flow exiting at the top of column (S1) is conveyed to the bottom of column (C1), at the feed level of the reaction gases into this column. The crude mixture obtained at the column bottom (6) is composed mainly of acrylic acid (7.73%), of the absorption solvent and of small amounts of heavier compounds than acrylic acid (maleic anhydride, furfuraldehyde, benzaldehyde, and the like). The content of light compounds is particularly low in this medium (acetic acid: 0.011%; water: 0.007%).

After a first condensation of the gas flow (3) exiting at the top of column (C1), the non-condensed vapours are conveyed to the bottom of the column for washing with water, countercurrentwise to the aqueous flow (2750 g/h). The aqueous solution obtained at the bottom of (L1) (4) assays 0.026% of acrylic acid and 0.345% of acetic acid.

Under these conditions, the performance of the (C1)–(S1) system is such that the degree of absorption of acrylic acid reaches 99.8% and the degree of removal of acetic acid 96.4%.

Example 2

A crude mixture (6) obtained at the bottom of column (S1), mainly comprising, in addition to the ditolyl ether solvent, 10.12% of acrylic acid and 0.06% of maleic anhydride, is conveyed to the bottom of the column (C3) at a temperature of 90° C. with a flow rate of 1166 g/h. The pressure at the top of column (C3) is regulated at $1.33 \times 10^4$ Pa (100 mm Hg). The heating of the boiler is adjusted so as to maintain a temperature of 170° C. in the bottom of column (C3). The temperature measured at the column top, at the level of the topmost plate, is 80.5° C. A 1.5% solution of p-methoxyphenol in acrylic acid is injected at a flow rate of 20.2 g/h at the top of the condenser. A portion of the distillate (7), after condensation (115 g/h), is conveyed to the top of the column. The distillate collected (127 g/h) exhibits an excellent purity with regard to compounds heavier than acrylic acid (0.03% of maleic anhydride, 0.017% of furfuraldehyde and less than 0.001% of benzaldehyde and of ditolyl ether). The flow (8) obtained at the column bottom (1058 g/h) is composed essentially of ditolyl ether and also assays 0.55% of acrylic acid and 0.06% of maleic anhydride.

Example 3

A flow (8) recovered at the bottom of column (C3), which comprises, in addition to ditolyl ether and the heavy products, 0.145% of acrylic acid and 0.07% of p-methoxyphenol, is conveyed (1000 g/h) at a temperature of 160° C. to the bottom of column (C4), which operates under a pressure of $6.66 \times 10^3$ Pa (50 mm Hg). The temperature at the level of the boiler is regulated at 191° C. and the set-point temperature for drawing off at the level of the 5th plate is set at 140° C. The product distilled at the column top (1.45 g/h), intended to be conveyed as feed of column (C3), is composed of 96.8% of acrylic acid and 3.2% of maleic anhydride and contains no trace of absorption solvent. The flow (10), drawn off as side draw-off (0.6 g/h), comprises 1.47% of acrylic acid, 54% of maleic anhydride, 30% of absorption solvent and 10.8% of p-methoxyphenol. Finally, the mixture (1) obtained at the column bottom, intended to be recycled at the top of column (C1), is mainly composed of the absorption solvent and of the heavy products from addition to acrylic acid, without any trace of acrylic acid (less than 0.005%) and with small contents of maleic anhydride (0.019%).

It will be noted, in this example, that the degree of removal of the maleic anhydride in the flow drawn off from the side of the column reaches 57% and that the loss of acrylic acid does not exceed 0.6% of the content of this monomer in the feed flow. In addition, the sidestream draw-off makes it possible to remove 10% of the p-methoxyphenol present in the feed of the column and thus to deconcentrate the solvent recovered at the bottom of (C4), which is intended to be recycled at the top of (C1).

Example 1a (Comparative)

Under the same conditions as Example 1, 3930 g/h of a solvent (1) composed of a eutectic mixture of diphenyl (23.5%) and of diphenyl ether (73.5%) is conveyed, at a temperature of 50° C., to the top of column (C1) and a reaction gas resulting from a catalytic reaction for the oxidation of propylene is conveyed to the bottom of this same column. This gas mixture (2) has an identical composition to that of Example 1 and feeds the column (C1) at the same temperature of 160° C. In addition, this column receives, at the bottom, the gas flow resulting from the top of column (S1).

The liquid obtained at the bottom of column (C1) (5) feeds the column (S1) at the top of the latter at a temperature of 120° C. 600 l/h of air, preheated to 50° C., are conveyed to the bottom of column (S1).

Under these conditions, the crude mixture (6) obtained at the bottom of column (S1) assays 5.76% of acrylic acid, 0.01% of acetic acid and 0.022% of water.

At the top of column (C1), the gas flow (3) is cooled in a cooler and then conveyed into the washing column, which receives, at the top, a flow rate of 2300 g/h of water. The mixture (4) of the condensate and of the aqueous flow obtained at the washing column bottom assays 2.32% of acrylic acid and 0.55% of acetic acid.

The degree of removal of acetic acid in the assembly (C1)–(S1) is 95% but the degree of absorption of acrylic acid remains limited to 81.8% (i.e. a loss of 19.2%).

Example 2a (Comparative)

A mixture from the bottom of column (S1) (6), mainly comprising the solvent, which is a eutectic mixture composed of 73.5% of diphenyl ether and 26.5% of diphenyl, with, in addition, 9.5% of acrylic acid and 0.06% of maleic anhydride, is conveyed, at a temperature of 90° C. and with a flow rate of 1164 g/h, to the bottom of the column (C3), which operates under a pressure of $1.33 \times 10^4$ Pa (100 mm Hg). The column bottom temperature is regulated at 160° C. A solution of p-methoxyphenol (1.5%) in acrylic acid is injected at a flow rate of 23.2 g/h at the top of the condenser. A portion of the distillate (7), after condensation (115 g/h), is conveyed to the top of the column. The main contents of heavy compounds in the distillate collected (126 g/h) are 0.05% of maleic anhydride, 0.03% of furfuraldehyde and 0.02% of benzaldehyde. The flow (8) obtained at the column bottom (1064 g/h) is composed essentially of the solvent and also assays 0.50% of acrylic acid and 0.06% of maleic anhydride.

This example shows that, for the same concentration of acrylic acid in the column bottom, the composition of heavy products in the distilled acrylic acid flow is higher than in Example 2.

Example 3a (Comparative)

1000 g/h of a mixture recovered at the bottom of column (C3), composed mainly of the heavy absorption solvent (eutectic mixture of diphenyl and diphenyl ether), of acrylic acid (0.69%), of maleic anhydride (0.06%), of hydroquinone (0.04%) and of low contents of heavy compounds from the addition to the double bond of acrylic acid, are conveyed to the base of column (C4), which operates under a pressure of $1.33 \times 10^4$ Pa (100 mm Hg). This mixture is preheated to a temperature of 180° C. before being conveyed into the boiler of the column. The temperature in the boiler is regulated at 182° C. The set-point temperature for drawing off the flow rich in heavy intermediate compounds, at the level of the 5th plate, is set at 135° C. A flow (6.4 g/h) composed of 97.1% of acrylic acid, 2.49% of maleic anhydride and 0.07% of absorption solvent is distilled at the column top at a temperature of 84° C. The flow drawn-off from the side at the level of the 5th plate (0.5 g/h) is composed of 62% of maleic anhydride, 29% of heavy absorption solvent and 5.3% of acrylic acid. Finally, a mixture is drawn-off at the column bottom composed essentially of the heavy absorption solvent and of the heavy compounds from the addition to acrylic acid, as well as 0.02% of acrylic acid, 0.016% of maleic anhydride and 0.038% of hydroquinone.

Under these conditions, the loss of acrylic acid in the flows (10) and (1) reaches 3.3% of the amount of monomer present in the flow (8) feeding the column (C4). The degree of reduction in the maleic anhydride, drawn-off from the side, is 48%. All of the hydroquinone inhibitor is found in the bottom flow of (C4).

Example 4 (Comparative)

1000 g/h of a flow composed of a eutectic mixture of diphenyl and of diphenyl ether comprising 0.31% of acrylic acid, 0.29% of maleic anhydride and 0.073% of p-methoxyphenol are conveyed into the base of a column (C4) operating under conditions identical to those of Comparative Example 3a. The flow drawn off from the side on the plate 5 (0.7 g/h), which assays 55.5% of maleic anhydride, comprises only 0.28% of p-methoxyphenol and this inhibitor is only present in the form of traces (0.004%) in the top flow (3.2 g/h). Virtually all the p-methoxyphenol is in the flow obtained at the column bottom (976.6 g/h), which assays 0.074% of this stabilizer.

It is noted in this example that, in contrast to Comparative Example 3a, carried out in ditolyl ether medium, the degree of removal of the p-methoxyphenol inhibitor in the side draw-off flow is negligible (0.3%) and is not sufficient to significantly deconcentrate with regard to this additive the solvent intended to be recycled at the top of (C1).

Example 5

In this example, a comparative evaluation is carried out of the efficiency of various polymerization inhibitors under the distillation conditions of the column (C3). In order to simulate the loop of solvent which is recycled numerous times in the process with the inhibitor, the experiments were carried out with total recycling, into the feed tank, of the column top and bottom flows combined beforehand.

The distillation column, with a height of 60 cm and a diameter of 38 mm, is equipped with a packing of multiknit type and with a thermosiphon boiler heated by an electrical element. The tests are carried out under a pressure of $1.33 \times 10^4$ Pa (100 mm Hg). The feed receiver (R1) of the column comprises 4800 g of a mixture composed of 10% of acrylic acid and 0.05% of the inhibitor to be tested, the remainder being the solvent, which is ditolyl ether. This mixture, preheated through an exchanger to a temperature of 100° C., is conveyed at a flow rate of 1200 g/h to the bottom of the column. The temperature in the boiler is regulated at 170° C. The column top temperature is 83° C. The vapours obtained at the column top are condensed in a vertical cooler and the condensed liquid is collected in a receiver (R2). From this receiver (R2), a pump conveys a portion of the condensed liquid into the top of the column with a reflux/flowing ratio of 2/1. An addition of 24 g/h of the inhibitor to be tested, as a 1.5% solution in acrylic acid, is carried out at the cooler top, in order to stabilize the distilled acrylic acid. The same flow rate of liquid is withdrawn from the flow exiting from the receiver (R2) and removed from the loop, in order to maintain a constant volume in the loop. The remaining distillate flow is mixed with the flow obtained at the column bottom and conveyed into the feed receiver (R1). It is calculated that, due to the addition of fresh stabilizer to the distillate, the initial content of inhibitor in the feed flow (0.05%) increases by 0.007% per hour.

When this experiment is carried out with phenothiazine as inhibitor, brown polymeric deposits along the column and at the top of the latter, as well as in the pipe conveying the reflux into the column top, are observed after operating for 19 hours. These deposits subsequently continue to increase, until the packing is completely blocked after operating for 65 hours.

The same experiment, under strictly identical conditions, was carried out with relatively light phenolic compounds (the boiling point of which is less than 270° C). The following inhibitors were tested independently:

p-methoxyphenol
2,6-di-tert-butyl-p-cresol
2,4-dimethyl-6-tert-butylphenol

In the three cases, no visible trace of deposit was observed after an operating time of 70 hours.

What is claimed is:

1. A process for the purification of acrylic acid obtained by catalytic oxidation of propylene, comprising extracting acrylic acid in an extraction stage by countercurrentwise washing of reaction gases containing acrylic acid with at least one heavy hydrophobic absorption solvent, and recovering purified acrylic acid from the solution obtained on conclusion of said extraction stage, wherein said at least one heavy hydrophobic absorption solvent is a hydrophobic aromatic compound having:
a boiling point at atmosphere pressure between 260° C. and 380° C.;
a crystallisation temperature of less than 35° C.; and
a viscosity of less than 10 mPa·s in a temperature range of 30–80° C., and
wherein said hydrophobic aromatic absorption solvent is not an ester, and is not a mixture of biphenyl and diphenyl ether.

2. A process according to claim 1, wherein said hydrophobic aromatic compound has a boiling point of between 270° C. and 320° C.

3. A process for the purification of acrylic acid obtained by catalytic oxidation of propylene, comprising extracting acrylic acid in an extraction stage by countercurrentwise washing of reaction gases containing acrylic acid with at least one heavy hydrophobic absorption solvent, and recovering purified acrylic acid from the solution obtained on conclusion of said extraction stage, wherein said at least one heavy hydrophobic absorption solvent is a hydrophobic aromatic compound having
a boiling point at atmosphere pressure between 260° C. and 380° C.;
a crystallisation temperature of less than 0° C.; and
a viscosity of less than 10 mPa·s in a temperature range of 30–80° C.

4. A process according to claim 1, wherein the at least one hydrophobic aromatic compound is represented by formula (I) or formula (II):

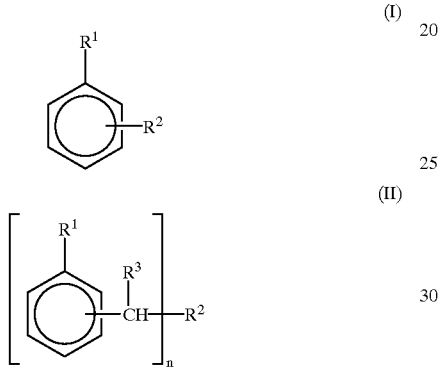

in which:
$R^1$ represents hydrogen, $C_1$–$C_4$ alkyl or cycloalkyl;
$R^2$ represents $C_3$–$C_8$ alkyl, cycloalkyl, —O—$R^4$, —O—Ph—($R^5$)—$R^6$ or —Ph—($R^5$)—$R^6$;
$R^3$ represents hydrogen or $C_1$–$C_4$ alkyl;
$R^4$ represents $C_3$–$C_8$ alkyl or cycloalkyl;
$R^5$ and $R^6$ each independently represent hydrogen or $C_{1-4}$ alkyl;
Ph represents a phenylic nucleous; and
n has the value 1 or 2; or
is represented by formula (III)

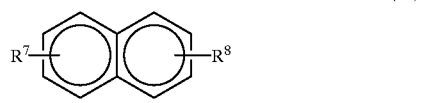

in which:
$R^7$ represents hydrogen or $C_1$–$C_4$ alkyl; and
$R^8$ represents $C_1$–$C_4$ alkyl.

5. A process according to claim 1, wherein said hydrophobic aromatic compound is ditoyl ether in the form of a single isomer or of a mixture of isomers.

6. A process according to claim 1, wherein the purification of acrylic acid is carried out, after the extraction stage, by distillation in the presence of a polymerization inhibitor or of a mixture of polymerization inhibitors which is lighter than said at least one heavy hydrophobic absorption solvent, exhibiting a difference in boiling point of greater than 15° C. in comparison to that of said absorption solvent.

7. A process according to claim 6, the polymerization inhibitor is p-methoxyphenol, 2,6-di-tert-butyl-p-cresol, 2,4-dimethyl-6-tert-butylphenol or a mixture thereof.

8. A process according to claim 1, wherein:
a distillation is carried out, in a distillation column (C3), of a flow (6) obtained at the bottom of an extraction column (C1), in which column acrylic acid is extracted by countercurrentwise washing of reaction gases with said at least one heavy hydrophobic solvent, said flow (6) comprising the heavy hydrophobic absorption solvent(s), acrylic acid and impurities with boiling temperatures greater than that of acrylic acid, said distillation is carried out under conditions to obtain a pure acrylic acid flow (7) at the top of said distillation column (C3), and acrylic acid is allowed to pass into a bottom flow (8);

the bottom flow (8) from said distillation column (C3) is conveyed as feed into the lower part of a further distillation column (C4), from the side of which is drawn off, on a plate situated between the feed and the column top, a flow (10) rich in maleic anhydride and impurities with boiling temperatures situated between that of acrylic acid and that of said heavy hydrophobic solvent or that of the lighter of the heavy solvents used as a mixture;

a flow (9) rich in acrylic acid is removed from the top of said further distillation column (4), which flow can advantageously be conveyed to the distillation column (C3); and a flow (1) comprising the heavy absorption solvent(s) and heavy impurities, with boiling temperatures greater than that of the said heavy solvent or of the lighter of the heavy solvents used as a mixture, is recovered at the bottom of the said further distillation column (4), which flow is recycled to the top of the extraction column (C1) for extraction of acrylic acid present in the reaction gases.

9. A process according to claim 8, wherein the flow obtained at the bottom of the column (C1) is freed from a portion of its residual light impurities, at the top of an additional column (S1), which can operate as a conventional distillation column equipped with a bottom reboiler or as a stripping column fed at the bottom with a gas, and a gas flow obtained at the top of the additional column (S1) still comprises acrylic acid and is conveyed to the extraction column (C1).

10. A process according to claim 8, wherein a flow (6) obtained at the bottom of the extraction column (C1), or at the bottom of the column (S1), is conveyed onto a plate situated in the lower half of the distillation column (C3) and that the operating conditions of the distillation column (C3) are chosen so as to obtain:
at the top, a flow (7) composed:
at least 95% by weight of acrylic acid;
the remainder of the flow (7) at the top is composed of heavy compounds including maleic anhydride, furfuraldehyde, benzaldehyde and traces of the heavy extraction solvent(s); and
at the bottom, a flow (8) composed of:
at least 95% by weight of the heavy solvent(s) and of the heavy impurities;
the remainder of the flow (8) at the bottom is composed of acrylic acid.

11. A process according to claim 8, wherein the flow (10) rich in maleic anhydride and heavy impurities is drawn-off from the side of the further distillation column (C4), at an intermediate plate situated above the feed between the lower quarter and the upper quarter of this column, and at a temperature whereby this flow (10) has of a concentration at least 20% by weight of impurities with boiling temperatures between that of acrylic acid and that of the extraction solvent or of the lighter of the solvents used as a mixture.

12. A process according to claim 8, wherein the flow (9) removal from the top of the further distillation column (C4) comprises:

at least 90% by weight acrylic acid; and the remainder is composed of impurities with higher boiling temperatures, and this flow is conveyed to the distillation column (C3) at the level of the main feed of the distillation column or at a level situated above said main feed.

13. A process according to claim 8, wherein, before recycling to the top of the extraction column (C1), at least a portion of the flow (1) obtained at the bottom of column (C4) is freed from its heavy impurities with boiling temperatures greater than that of the solvent or solvents by distillation or extraction with the aid of a solvent, optionally used in addition to a thermal dissociation treatment which may optionally involve a catalyst.

14. A process according to claim 8, wherein distillation is carried out:

in the distillation column (C3), under a pressure of $2.66 \times 10^3 – 3.33 \times 10^4$ Pa, at a top temperature of 40–120° C. and at a bottom temperature of 120–230° C.; and in the further distillation column (C4), under a pressure of $2.66 \times 10^3 – 3.33 \times 10^4$ Pa, at a top temperature of 40–120° C., at a bottom temperature of 120–230° C. and at a side draw-off temperature of 40–180° C.

15. A process according to claim 6, wherein said difference in boiling point is greater than 20° C.

16. A process for the purification of acrylic acid obtained by catalytic oxidation of propylene, comprising extracting acrylic acid in an extraction stage by countercurrentwise washing of reaction gases containing acrylic acid with at least one heavy hydrophobic absorption solvent, and recovering purified acrylic acid from the solution obtained on conclusion of said extraction stage, wherein said at least one heavy hydrophobic absorption solvent is a hydrophobic aromatic compound having:

a boiling point at atmosphere pressure between 260° C. and 380° C.;

a crystallisation temperature of less than 35° C.; and a viscosity of less than 10 mPa·s in a temperature range of 30–80° C., and wherein said hydrophobic aromatic absorption solvent is not a heavy carboxylic acid having a melting point of less than 30° C. and a boiling point of greater than 160° C., and wherein said hydrophobic aromatic absorption solvent is not a mixture of diphenyl and diphenyl ether.

17. A process for the purification of acrylic acid obtained by catalytic oxidation of propylene, comprising extracting acrylic acid in an extraction stage by countercurrentwise washing of reaction gases containing acrylic acid with at least one heavy hydrophobic absorption solvent, and recovering purified acrylic acid from the solution obtained on conclusion of said extraction stage, wherein said at least one heavy hydrophobic absorption solvent is a hydrophobic aromatic compound having:

a boiling point at atmosphere pressure between 260° C. and 380° C.;

a crystallisation temperature of less than 35° C.; and a viscosity of less than 10 mPa·s in a temperature range of 30–80° C., and wherein said hydrophobic aromatic absorption solvent does not yield impurities, due to hydrolysis, which will react with acrylic acid to form esters, and wherein said hydrophobic aromatic absorption solvent is not a mixture of diphenyl and diphenyl ether.

* * * * *